United States Patent
Eberl et al.

(10) Patent No.: US 6,523,955 B1
(45) Date of Patent: Feb. 25, 2003

(54) METHOD FOR IMPROVING OPTIC PERCEPTIVE FACULTY BY MODIFYING THE RETINAL IMAGE

(75) Inventors: Heinrich Alexander Eberl, Probstried; Guenter Abersfelder; Helmut Grantz, both of Sindelfingen; Thorsteinn Halldorsson, Munich; Horst Schmidt-Bischoffshausen, Neubiberg; Stefan Uhl, Stuttgart, all of (DE)

(73) Assignee: Heinrich A. Eberl, Probstried (DE)

( * ) Notice: Subject to any disclaimer, the term of this patent is extended or adjusted under 35 U.S.C. 154(b) by 0 days.

(21) Appl. No.: 09/462,440

(22) PCT Filed: Jul. 3, 1998

(86) PCT No.: PCT/DE98/01840

§ 371 (c)(1),
(2), (4) Date: May 1, 2000

(87) PCT Pub. No.: WO99/03013

PCT Pub. Date: Jan. 21, 1999

Related U.S. Application Data

(63) Continuation-in-part of application No. 09/230,996, filed on Oct. 12, 1999, now Pat. No. 6,227,667.

(30) Foreign Application Priority Data

Jul. 7, 1997 (DE) .......................................... 197 28 890

(51) Int. Cl.$^7$ .................................................. G02C 5/14
(52) U.S. Cl. ........................................................ 351/211
(58) Field of Search ................................. 351/205, 206, 351/208, 209, 210, 211, 212, 221; 382/103, 128; 345/8; 359/630

(56) References Cited

U.S. PATENT DOCUMENTS

| | | | |
|---|---|---|---|
| 4,213,678 A | 7/1980 | Pomerantzeff et al. | 351/7 |
| 5,467,150 A | 11/1995 | Isogawa et al. | |
| 6,227,667 B1 | 5/2001 | Halldorsson et al. | 351/206 |
| 6,325,513 B1 | 12/2001 | Bergner et al. | 351/221 |
| 6,369,953 B2 | 4/2002 | Melville et al. | 359/630 |

FOREIGN PATENT DOCUMENTS

| | | |
|---|---|---|
| DE | 196 31 414 A1 | 2/1998 |
| WO | WO 92/03187 | 3/1992 |
| WO | WO 96/36036 | 11/1996 |

*Primary Examiner*—George Manuel
(74) *Attorney, Agent, or Firm*—Crowell & Moring LLP

(57) ABSTRACT

In an electronic image enhancement system, a reflex image is scanned in the interior of the eye. After modification by a processor, the image is projected back into the eye along the same path, and aligned in registration with the original scanned image. An elliptical scan pattern is used.

44 Claims, 3 Drawing Sheets

CONCENTRIC
CIRCLE SCAN

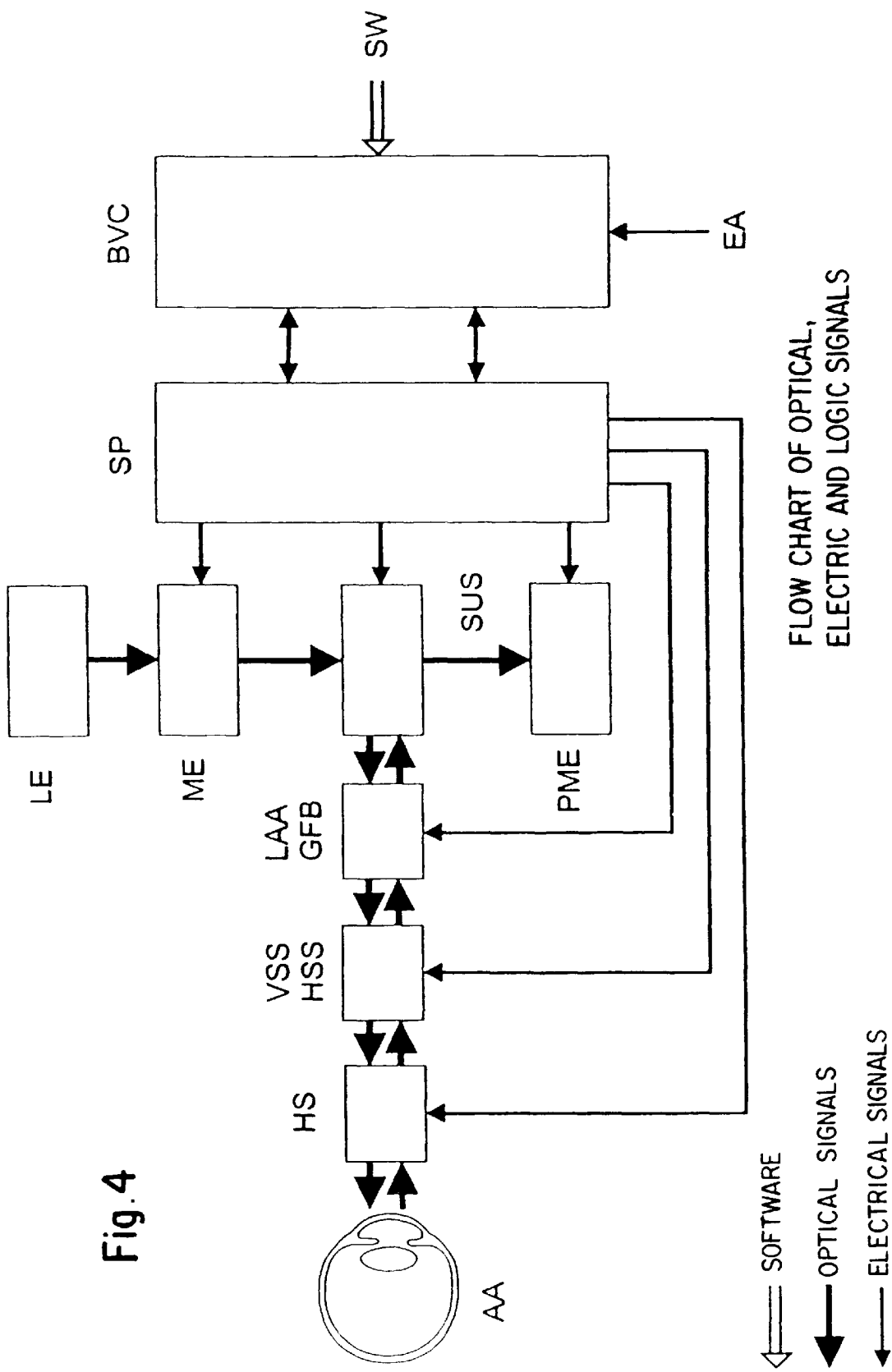

METHOD FOR IMPROVING OPTIC PERCEPTIVE FACULTY BY MODIFYING THE RETINAL IMAGE

This application is continuation-in-part of U.S. patent application Ser. No. 09/230,996, now issued as U.S. Pat. No. 6,227,667.

BACKGROUND AND SUMMARY OF THE INVENTION

The invention relates to spectacles which, utilize a specular reflection on their interior side to record electronically a retinal reflex image formed in the eye. This image is modified by means of a computer and, by means of an illumination device and a back reflection, is physiologically without delay by way of the same spectacles superimposed on the original image such that an improved visual impression is created.

The use of opto-electronic spectacles for the reflection of computer-generated images into the eye, which has the name "cyberspace" or "virtual reality", is increasing very rapidly. This technique has a wide range of benefits for an application in the entertainment industry as well as in various fields of industry, traffic and medicine, and its spread and significance will constantly increase with the availability of increasingly faster image processing computers.

The application by means of closed non-transparent glasses, in the case of which images are provided to the eye by miniaturized cathode ray tubes or liquid-crystal matrices by way of mirror systems or glass fiber systems, is most common. It is a particular advantage of this technique to couple by means of a moving three-dimensional imaging, the image sequence or the action with different movements of the wearer of the spectacles. Thus, a changing of the viewing direction as the result of the movement of the head or the change of the perspective is simulated as the movement progresses. The movements of the arms and the fingers of the wearer of the spectacles can be entered into the image by means of sensors in order to permit him to directly intervene in the action.

In newer systems called "augmented reality", the wearer of the spectacles, by means of partially transparent spectacles, can view the environment as well as an image of cameras, which is reflected in by way of the spectacles, of the same scene or of other image contents by means of a miniaturized monitor at the helmet. A well-known variant of this process which is called a "helmet-mounted display (HMD)" has already been introduced for the guidance of combat planes.

However, several problems have become known concerning this technique which are the result of the function of the sense of sight and await improved technical solutions. In the case of closed spectacles and a rigidly coupled monitor or monitor image, when the wearer of the spectacles moves his head, the scene moves along in the same direction, which unnaturally is in conflict with his visual habits. As the result of the imaging of the eye, he is accustomed to the fact that the scene extends precisely in the opposite direction. So far, this problem has been solved only incompletely by means of the cumbersome measuring of the head movement and of the eyeball by means of external angle-of-rotation sensors, by a corresponding image processing and by the tracking of the generated image.

As the result of the adaptation movements of the eyeball, which originate from so-called vestibular ocular reflexes (VOR) of the ear canal system and are used for holding the fixation point during movements of the head, the eye itself is capable of roughly stabilizing the retinal image. The fine adjustment takes place by means of the image as the reference. This image tracking is additionally used by the eye for adapting the VORs of a dynamic eye alignment.

This means that a superimposing of outside images can provide a realistic impression of the image only when they are coupled to the real retinal image.

In the case of closed spectacles, it is attempted to use the image of the blood vessels (ocular fundus) as the reference (retina tracking). However, this supplies an only insufficient resolution and is suitable only for monocular viewing (see, for example, E. Peli, "Visual Issues in the Use of a Head-Mounted Monocular Display", *Optical Engineering,* Vol. 29, No. 8, Page 883 (1990). A simultaneous stabilization in both eyes of images by means of these is virtually impossible because of the different alignment of the eyes. In addition to the deterioration of the image quality, the conflict between the vestibular and the visual information frequently leads to motor disturbances ranging to seasickness. These problems of the existing technology are described, for example, in the overview article by E. Peli, "Real Vision & Virtual Reality" in *Optics & Photonics News,* July 1995, Pages 28-34.

It is an object of the invention to solve the problems involving image stabilization in the case of the superimposing of outside images by means of the real image.

The invention is based on the older German Patent Application 19631414 with the title "System for Detecting Retinal Reflexes and the Superimposing of Additional Images in the Eye". In this application, a system is described by means of which the retinal reflex image is detected by means of a confocally imagining, two-axis scanning system by way of the reflection of the interior side of partially transparent and correspondingly curved spectacles serially by means of a high-sensitivity photodetector.

It is suggested there to serially project the improved image on the retina by means of lasers and a beam splitter via the same light path in the reverse direction of the taken image.

Furthermore, it also becomes possible to additionally superimpose other images on the retina.

This technique basically solves the above-mentioned problems, but concrete implementations and applications are not indicated. It is the fundamental idea of the new invention to use this process for improving the perceptivity of the eye. The physical-technical problems which must be solved for this purpose are the result of the physiological characteristics of the eye and the constantly varying illumination conditions in the environment. Because of the variable light conditions and the different optical tasks, the eye is a very dynamic sense organ with respect to its basic functions. It adapts itself to the variation of the intensity of the background illumination for 12 decades. It changes from colored sight in daylight to purely black/white sight at night. Light in the wavelength range of from 400–1,500 nm is transmitted by the eye and imaged on the retina. In this case, only light in the range of from 400 nm to 750 nm is perceived; that is, the infrared light in the range of from 750 to 1,500 nm, which is very bright in the case of an exterior as well as an interior illumination, remains unutilized for the visual perception.

The eye horizontally and vertically covers an angular range of approximately 1000. However, the image resolution decreases very rapidly with the angular distance from the visual axis. The attentive momentary vision is limited to a central angular area of only +/−5°, and the "sharp" vision, for example, when reading or driving a car, is limited to the very small central angular range of +/−0.5°. In addition, various movements of the eye also take place constantly. This results in consequences which, under certain circumstances, impair the perceptivity of the eye and are to be improved within the scope of the invention:

Adaptation
accommodation
sharpness capacity
defective vision
age-related reduced capability, and
movement dynamics.

It is an object of the present invention to suggest an arrangement which, similar to the eye, has very variably designed basic functions and is adapted to the requirements of the seeing process but simultaneously also takes into account and utilizes the special physiology and dynamics of the eye and the varying illumination conditions of the environment as well as the invisible IR-range. This can be achieved only insufficiently by means of the scanning variants (serial grid scan, serial spiral scan) indicated in the earlier application. This concerns the scanning pattern of the image-taking of the retinal reflex as well as the back-projection of the laser image into the eye.

A basic problem of the serial image scanning in contrast to the parallel image scanning is the short dwell time of the scanner in each image pixel. A uniform scanning of, for example, 0.5 million image points during a scanning time of 40 ms means an integration time of only 0,08 μs, that is, 80 ns, in each image point. In comparison, the parallel time integration of all image points of the eye itself is 10–20 ms.

As known from the use of lasers for detecting the retinal structure of the eye in the so-called laser scanning ophthalmoscopes, a laser power of approximately 40 μW is required in order to achieve during a laser scan a signal-to-noise ratio of 17 from one image pixel (see, for example, A. Plesch, U. Klingbeil and J. Bille, "Digital Laser Scanning Fundus Camera" *Applied Optics,* Vol. 26, No. 8, Pages 1480–1486 (1987)). Converted to the larger surface, this would correspond to an intensity of irradiation in an image of an extensive source on the retina of 40 W/cm², which corresponds to the intensity of irradiation of bright spotlights or the sun on the retina; that is, it is only by means of the grid scan, that relatively bright sources can be recorded on the retina with a good signal-to-noise ratio. In order to detect the imaging of weaker sources on the retina, the sensitivity must be increased significantly.

However, for detecting the retinal reflex, the serial image scanning has the decisive advantage of a better suppression of scattered light, of a simpler detecting lens system and of the possibility of an exact reversal of the beam path during the image back-projection by means of a laser and, for these reasons, should be retained also in this application. However, an extension of the dwell time can be achieved by changing the scanning pattern.

Because of the non-uniform distribution of the photo-receptors, with the highest density of the cones for the sharp vision in the center of the retina and the opposite course of the small rods for the out-of-focus but light-sensitive night vision, the grid scan is by no means the optimal scanning pattern. A scanning pattern which is adapted to the seeing process, for day vision, should become increasingly slower and denser in the direction toward the center; and for an adaptation to night vision, it should be precisely the reverse.

In addition to the dwell time, the received signal can be influenced by changing the spot size of the scan and thus also the image resolution.

The number of signal photons N, which are recorded by a scanning recording unit from the retina per image pixel can be calculated according to the following formula:

$$N_s = (BT\Delta\lambda\tau)(A_o R)(S/2\pi)(A_p/D^2)(1/\epsilon)$$

wherein

B=the spectral irradiation intensity on the retina
T=the optical transmission from the retina to the photo-detector
τ=the integration time in an image pixel on the retina
$A_o$=the surface of the image pixel
R=reflectivity of the image pixel
Δλ=spectral width of the receiving signal
$A_p$=pupillary surface
D=distance from pupilla to retina
S/2π=the angular distribution factor of the optical back-scattering of the retina
ϵ=energy of a photon at the detecting wavelength As illustrated by this formula, stronger signals, that is, a larger number of signal photons can be obtained by the following measures at the detecting instrument:

Extension of the dwell time τ of the scan in the individual image points,
enlargement of the scanning spot $A_o$ on the retina,
enlargement of the spectral bandwidth Δλ.

The invention suggests the scanning of the retina in a sequence of concentric circles (the center of the circle is equal to the fovea centralis) whose radius is enlarged and reduced successively. This type of scanning is called a circle scan. Because of the rotational symmetry of the eye lens and of the pupil about the visual axis and the rotationally symmetrical distribution of the photoreceptors in the retina, the circle scan is optimal.

The invention also suggests that an identical circle scan is used for the detection of the retina reflex from the environment and the image projection by means of the laser. Since, in the case of the circle scan from the outside to the center, after the reaching of the center, the scanning axis extends backward along the same path, the detection may optionally be used in the case of the scan to the center and the projection may be used from the center to the outside, or the detection may be used for the entire scanning process and the projection may only be used in a second one.

In the case of a constant deflection of scanning mirrors in two directions (Lissajou-Figur), during the circle scan, a slowing-down of the dwell duration necessarily takes place in the direction of the center. However, the invention provides that, for day vision, the scan duration of adjacent circles be additionally slowed down depending on the illumination conditions and can even be accelerated for night vision.

Because of the non-uniform distribution of the cones over the retina with a density in the center which is by more than two decades higher, the scanning rate (dwell duration per image point) in this area can be increased by this factor, 100.

For the night vision with a higher distribution of the small rods with an increasing radius, it is useful for the dwell time to decrease to a similar degree in the opposite direction toward the outside.

As known to the person skilled in the art, a circle scan can be implemented in an analog control by means of periodically swinging orthogonal scanning mirrors or in a digital control, by an approaching of the circular track with a large number of straight routes. The third alternative is the use of programmable algorithms of analog control signals which can be digitally called and are best suited for these variable conditions.

So that the receiving signal can be additionally increased also by the enlargement of the scanned image spot proportionally to its surface, the invention also provides that the momentary image pixel size on the retina can be variably adjusted in addition to the scanning rate.

With the change of the image spot size, the image resolution is also adapted corresponding to-the situation. In addition to changing the scanning surface, the resolution can also be adjusted by the variable radius jump of the scanning radii.

By means of an enlargement of the scanning image pixel of, for example, 10 $\mu$m to 100 $\mu$m, the image resolution, for example, of approximately 2 to 20 arc minutes (resolution range of reading and viewing) is reduced by a factor 10; the received signal is simultaneously increased by a factor 100.

As known to the person skilled in the art, during the confocal scanning, the image resolution is determined by the diaphragm diameter in the intermediate focus in front of the photodetector and can be adjusted by its change. The invention provides that liquid-crystal diaphragms or electro-optical diaphragms are used for this purpose, so that this adjustment can be carried out as rapidly as possible, that is, within one scanning cycle.

Since the time sequence of the scanning and the size of the image pixel during the detection and the projection should be as identical as possible, the invention suggests that the change of the scanning sequence and the diaphragm control in the projection channel be the same as in the detection channel. The variation of the optical integration time and the image pixel surface can then be compensated in the projection channel by the corresponding variation of the transmission power of the laser.

Furthermore, the level of the receiving signal depends on the spectral bandwidth of the receiver and can be increased by its widening. The invention provides that in the range of the bright daylight vision (photoptic vision), a splitting of the beam path into the color channels red-green-blue, each with a spectral width of approximately 100 nm, which corresponds to the color sensitivity of the eye, can be carried out. This permits a true-color image taking and, by means of corresponding three-color lasers, a colored back-projection into the eye.

In a low illumination of the environment, in which the colors are no longer perceived by the eye (scotopic vision), the invention provides the combining of all channels to one single (black/white) receiving channel without a color resolution. Furthermore, the invention provides that this receiving channel comprises not only the visible range of from 400–700 nm but, in addition, the close infrared range of from 700–1,000.

This has the following advantages for increasing the receiving signal in a low background illumination:

Between 400–1,000 nm, the eye has the full transparency and images a comparable image between 700–1,000 nm as between 400–700 nm;

the degree of reflection of the retina between 700–1,000 nm amounts to R=10–20% in comparison to R=3–5% between 400–700 nm;

photodetectors with a high quantum efficiency, such as photomultipliers and silicium avalanche diodes, are available over the whole spectral range of from 400 to 1,000 nm;

incandescent bulbs, which are used for the interior illumination of buildings, or outside, for the lighting of streets and in the case of vehicles, radiate 10 times more light between 700–1,000 nm than between 400–700 nm.

the reflectivity of the vegetation in nature is by a factor 5–10 higher between 700–1,000 nm than between 400–700 nm.

As illustrated by these examples, in low illumination (night vision), another increase of the receiving signal by a factor 100 can take by place by expanding the spectral range.

The expansion of the spectral range can either be fixedly installed in each instrument or can be designed to be variable by changing spectral filters. If a colored representation is not required, it is useful to use green laser light for the back-projection into the eye because of the extreme sensitivity and contrast perception of the eye with respect to this color.

Additional methods for the signal improvement, which can be used here, are the integration of several successive images and the image correlation, for example, images of both eyes.

On the whole, as the result of the variation of the two parameters—the dwell time of the scan in the image pixels and the size of the image spot—with the addition of the infrared range and the use of image correlation, the complete dynamics of the receiving signals can be detected over seven decades.

In the case of a complete optical transmission of the receiving channel of T=0.2 (see above formula), the receiving range of this dynamic detection system comprises irradiation intensities on the retina between $10^{-5}$ W/cm$^2$ and 100 W/cm$^2$, which comprises the range of the typical inside and outside luminosity.

Because of the slow and fast eye movements, it is necessary to design the scanning system such that it constantly follows the change of the axis of vision through the spectacles; that is, that the axis of symmetry of the image scanning during the detection as well as during the projection, is identical with the axis of vision.

For achieving this object, the invention provides that a centering of the circle scan on the pupil of the eye is carried out before and after the scanning of the retinal reflex and the image projection into the eye. In this case, the largest scanning angle of the circle scan is selected such that, if the axis of symmetry of the scan deviates from the axis of vision, the exterior surface of the eyeball, the sclera with the iris and the opening of the pupil, is scanned by the circle scan. Since these parts of the eye, which are well illuminated by the exterior light, are not imaged-sharply but diffusely in the intermediate image plane of the photodetector, the receiving signal supplies no image information but an integral indication of the optical backscattering capacity of the original pattern.

If the receiving signals are compared with one another for equally long time sections, for example, quadrants, from each circle, they will only be of the same level if the axis of the circle scan is identical with the axis of the eye (vision axis). Because of the different backscattering from the sclera, the iris and the opening of the pupil, signal differences then represent a measurement concerning the amount of deviation of the axis and its direction. After a scaling of the entire signal by way of each circle, these deviation signals can be used for adjusting the zero position of a next circle scan (bias). Thus, an original deviation of the axes can be reduced with each circle scan, until it becomes imperceptibly small when the circle scan dips through the opening of the pupil (pupil tracking).

Other objects, advantages and novel features of the present invention will become apparent from the following

BRIEF DESCRIPTION OF THE DRAWINGS

FIG. 4 is a block diagram which shows signal processing according to the invention.

DETAILED DESCRIPTION OF THE DRAWINGS

As an alternative to the use of ambient light, the invention provides that also by means of the active illumination of the laser projection into the eye, a pupil tracking in the outer areas of the circle scan can be carried out, with a simultaneous signal analysis in the detection channel, as described above.

The invention also provides that, also during the laser image projection, the light backscattered from the environment as well as from the laser is detected and analyzed. This simultaneous detection of the retinal reflex from the environment and the subsequently processing laser image projection makes it possible to constantly examine the degree of the overlapping and the time-related synchronization of both images, to detect possible differences as image interferences (Noire-pattern), in order to then subsequently compensate these by correction signals.

The detection and projection technique in the sense of the invention can either be carried out on one eye of the viewer or on both eyes simultaneously independently of one another. Because of the stereoscopic vision of both eyes, in the latter case, a three-dimensional image detection and image display is implemented.

It is not easily understandable that the detection of a faultless and distortion-free reflex image of the environment from the retina by means of spectacles which can neither be adapted in their optical characteristics individually to each viewer, nor can be disposed in a completely stable manner on the viewer's head. The solution in this respect according to the invention consists, first, of the relatively low optical demands on the serial confocal point scan in comparison, for example, with a surface-type imaging from the eye; secondly of the complete dynamic adaptation of the optical beam path of the scanner by way of the spectacles into the eye, which each time takes into account the spontaneous movements of the eye and of the spectacles themselves; and third in the exact reversal of the beam path between the detection and the projection and the short time duration between these operations. For adjusting the scan through the eye also in the case of the different eye movements, two scanning elements are used and one correction mirror which may also be adjustable.

Figure 2:
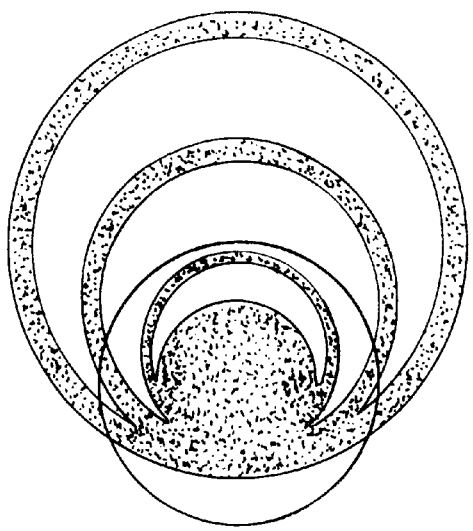
FIG. 2 represents the search mode for the centering of the scan through the pupil of the eye.
Figure 1:
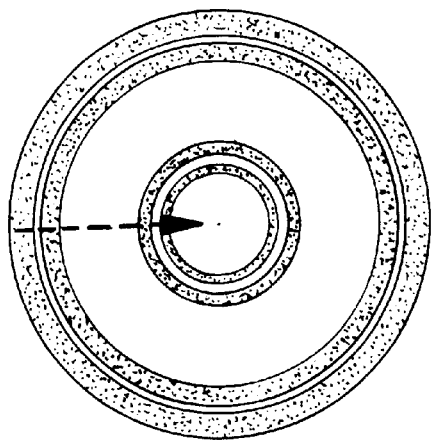
FIG. 1 is a schematic view of the concentric scanning operation in the adjusted system.
Figure 3:
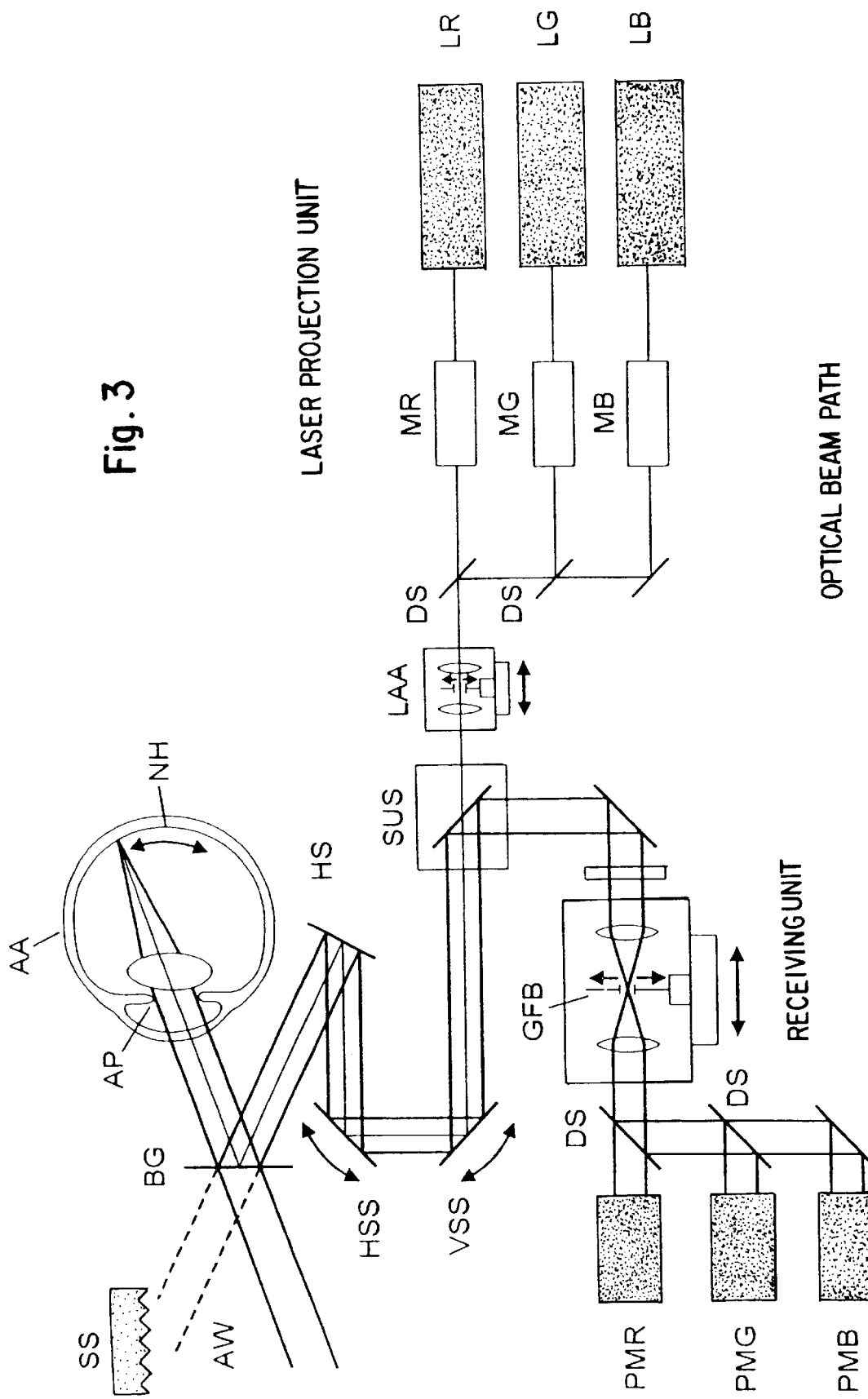
FIG. 3 is a schematic depiction of the optical viewing system according to the invention.

FIG. 3 is a schematic overview of the whole system. The retina of the eye NH is scanned by means of the focussed beam. Here AA represents the eyeball and AP represents the pupil of the eye. The semireflecting spectacles are marked BG.

The beams passing through from the environment are focussed on the retina. The retina is simultaneously scanned in a punctiform manner, in which case the scanning beam in the transmission through the spectacles is always directed against a radiation sink. The circle scan is carried out by means of the biaxial scanning elements HSS and VSS. By means of the auxiliary mirror HS, which may be actively adjustable, the direction of incidence and the position of the beam on the interior surface of the spectacles BG is adjusted. By means of the beam switch SUS, the illuminating laser beam can be permitted to pass through either by means of a central bore and the receiving beam, which usually has a significantly larger diameter, can be reflected into the receiving unit and be guided in different directions,or an actively switching mirror element can be used which switches between receiving and transmitting.

The receiving unit may consist, for example, of three separate receiving channels for the primary colors red, green and blue or other wavelength ranges, for example, in the close infrared range. The beam path of all spectral channels is placed onto one axis by means of dichroitic mirrors DS. For the adjustment of the spot size of the scanning beam on the retina and for the possible precision correction of the optical axis, an actively adjustable visual field diaphragm GFB is used.

The transmitting unit may be made, for example, of three lasers with the primary colors red LR, green LG and blue LB. Before the beam combination on one axis by means of dichroitic mirrors DS, the individual beams are either modulated externally by means of image modulators MR, MG and MB or more simply directly by way of the excitation current of the laser emission. The size and the position of the laser scanning spot on the retina is by means of an actively controllable diaphragm LAA which is adjusted in the intermediate focus of two lenses in the beam path. As the receivers for the scanning of the retinal reflex image, for example, photomultipliers are suitable which alternately, at very weak optical signals automatically switch over into a photon-counting operation and in the case of strong signals, automatically switch over into a current measuring operation. The use of avalanche photodiodes as receivers is also conceivable.

Semiconductor lasers or miniaturized solid-state lasers are provided as light sources for the back-projection of the images into the eye and have a low continuous wave power (<300 $\mu$W) and cannot endanger the eye. By using semiconductor lasers, the image modulation could be carried out directly by way of their current supply system. So that all colors are produced, it is recommended to use three lasers with the primary colors red, green and blue. As shown by the known color triangle of the human sense of vision, all other colors as well as the non-colors gray and white can be formed by the color summation of monochromatic laser lines of these colors. The invention also contains the possibility of the use of individual colors as a monochromatic solution.

As illustrated in FIG. 4, the invention provides a signal processor SP which electronically processes the direct image from the retina and synchronously coordinates all functions of the system as well as those of scanners VSS/HSS, of the auxiliary mirror HS and the laser spot adjustment LAA and the size of the field of vision diaphragm GFB. The image processing computer BVC will then take over the image perceived by the eye or images of other technical sensors which are fed to the computer by way of an external connection EA, and will process them according to a defined software SW before they are modulated by means of the signal processor onto the laser beams as an image signal. FIG. 4 illustrates the flow of the optical and electric as well as the software signals separately. The complete laser unit is called DE; ME is the modulation unit; PME is the complete receiving unit; and SUS is the beam switching device between the transmitting and receiving unit.

In addition to processing the current image processed by the computer and projecting it into the eye and fusing it with the original image, the laser projection also permits outside images, which are fed to the computer from the outside, to be synchronously superimposed on the outside image in the eye. If the time period between the taking of the image and the projection is correspondingly short in comparison to the fast eye movements, the eye will no longer perceive any interruption of images, as during the viewing of a television screen.

The separate but simultaneous image scanning on both eyes also detects the perspective difference of both images. Since these are retained during the laser back-projection in both eyes, a restoring of the spatial vision is ensured.

Currently, the components used in the invention are available in a largely miniaturized construction and at reasonable cost. For the scanning of the circular figures, miniaturized tilting mirrors can be used. A second possibility for producing the circular figures is the use of camera wedge scanners which are designed for a beam path in the transmission. The continuous beam is broken by each of the wedges about a fixed angle. The whole deflection angle can then, as the result of a fixed rotation of the camera wedges with respect to one another, be continuously adjusted until zero is reached. In the case of a common rotation of the camera wedges at a fixed rotating frequency, the deflected beam will then describe a circular track. A third possibility is the use of acousto-optical deflecting units which offer the advantage of a low time lag and of a fast deflection. The variably adjustable auxiliary mirror HS will preferably be a mirror which can be adjusted in two axes by means of a microactuator system.

For adjusting the laser spot size and the receiving visual field, micromechanical actuators are preferably used, as used also, for example, in the wide-spread laser printers and CD players.

The beam switching unit and the scanner can be housed in a simple frame of the spectacles. By means of glass fiber conduction, the laser projection unit can be accommodated in a small housing, for example, of the size of a pocketbook with a battery supply. The data exchange with an externally fixedly installed image processing computer can take place either by way of radio waves or infrared radiation. All elements of the system of the invention according to the current state of the art can therefore carried by a person without effort, and the wireless image data exchange with the external computer would permit his unlimited freedom of motion.

As in the earlier application No. 19631414.3 of the inventor, this type of opto-electrotonic spectacles can be used for many different purposes: Taking of images of the outside world, their processing, back-projection and fusing with the original image in the eye, as, for example, for improving the vision when driving a vehicle or as a visual aid for persons whose vision is impaired.

Superimposing of images of other image taking systems, for example, of the same scene in other spectral ranges onto the direct image in the same applications in which currently or in the future the helmet-mounted display is used.

Superimposing of virtual images which are produced only by the computer in the same or future applications of the "virtual reality" or "cyberspace" image projection.

What is claimed is:

1. A computer assisted viewing apparatus, comprising:
    a scanner system for scanning a reflex image in an interior of an eye;
    processing means for modifying said image; and
    means for projecting said image back into the eye along the same path followed by the scanner system;
    wherein said scanner system performs an elliptical scan.

2. The apparatus according to claim 1, further comprising means for determining outside edges of a pupil of the eye;
    wherein the elliptical scan is used to adjust and canter the scanner system, without additional external sensors.

3. The apparatus according to claim 2, wherein scanning duration is adapted to a required resolution, detection time and exposure time.

4. The apparatus according to claim 3, wherein the size of a scanning spot of the scanner system is dynamically adaptable to varying environmental conditions.

5. The apparatus according to claim 3, wherein track spacing of scanning tracks of the scanner system is dynamically adaptable to varying environmental conditions.

6. The apparatus according to claim 1, wherein a scanned image is spacially and temporally synchronized with the back-projected image.

7. The apparatus according to claim 1, wherein the size of a scanned area is adaptable to requirements of various applications.

8. The apparatus according to claim 1, wherein a scanned image is brightened by said processing means and is then projected back into the eye.

9. The apparatus according to claim 8, wherein a scanned image is projected in a wavelength range other than the wavelength at which it was taken.

10. The apparatus according to claim 9, wherein radiation of the scanned image is evaluated in a wavelength range outside the perception range of the eye, and is transformed into the visible range.

11. The apparatus according to claim 8, wherein the scanned image is brightened to such an extent that black-white vision information which was originally recognizable by the eye is transformed into color information.

12. The apparatus according to claim 8, wherein the scanned image is brightened by the processing means such that the physiological brightness sensitivity is displaced into a less sensitive region.

13. The apparatus according to claim 1, wherein a scanned image is sharpened in the processing means by computing and modulating of projection by way of a suitable algorithm, such that defective vision of the eye is compensated.

14. The apparatus according to claim 1, further comprising an external sensor for determining the position of a pupil of the eye, for adjusting the scanner system.

15. The apparatus according to claim 14, wherein an image content of a scanned image is evaluated in order to activate external reactions and control functions.

16. The apparatus according to claim 15, wherein the image contents are compared along two viewing axes.

17. The apparatus according to claim 16, wherein an image content of the forea centralis of both of said eyes is compared.

18. The apparatus according to claim 17, wherein the position of pupils and the image contents of the forea centralis of both of said eyes are used for determining a visual axis for distance determination by triangulation.

19. A The apparatus according to claim 18, wherein the image information of the eye is used for determining absolute brightness of the environment.

20. The apparatus according to claim 19, wherein the image information of the eye is used for determining absolute color temperature of the light.

21. The apparatus according to claim 15, wherein the position of the pupils of two eyes is compared.

22. The apparatus according to claim 1, wherein the system is used for determining pupil size.

23. The apparatus according to claim 1, wherein the elliptical scan extends from the outside toward the inside.

24. The apparatus according to claim 1, wherein the elliptical scan progresses from inside toward an outside thereof.

25. The apparatus according to claim 1, wherein the elliptical scan comprises a circular scan.

26. The apparatus according to claim 1, wherein said scanner system scans said eye in a sequence of successively larger or smaller ellipses.

27. A method for assisted viewing, comprising:
using a scanner to scan a reflex image in an interior of an eye and to generate scanner signals characteristic of said reflex image;
processing said scanner signal to modify said image; and
projecting said image back into the eye along the same path followed by the scanner;
wherein said scanner scans said reflex image according to an elliptical scanning pattern.

28. A method for assisted viewing according to claim 27, wherein the projected image is aligned in spacial and temporal registration with the scanned reflex image.

29. A method for assisted viewing according to claim 28, wherein said processing includes modifying at least one of an intensity and a frequency of radiation in said image.

30. A computer assisted viewing apparatus, comprising:
a scanner system for scanning a reflex image in an interior of an eye;
processing means for modifying said image; and
means for projecting said image back into the eye along the same path followed by the scanner system;
wherein said scanner system scans said eye in a sequence of successively larger or smaller ellipses.

31. Apparatus for improving optical perception in an eye, comprising:
scanning means for acquiring and modifying a retinal image in said eye;
wherein said scanning means scans said eye in a sequence of successively larger or smaller ellipses.

32. Apparatus for improving optical perception of an image in an eye, comprising:
projecting means for projecting said image into the eye;
wherein said projecting means projects said image according to an elliptical scanning pattern.

33. The apparatus according to claim 32, wherein said elliptical scanning pattern comprises a sequence of successively larger or smaller ellipses.

34. A method of capturing ocular reflex signals, comprising:
serially projecting pixels of laser light onto the retina of an eye;
capturing a portion of laser light reflected from said retina; and
simultaneously serially capturing a retinal reflex image of an ambient scene.

35. The method of claim 34, further comprising:
generating deviation signals based on said captured laser light;
correcting, based on said deviation signals, a zero position for a scan pattern of a subsequent serial capture of a retinal reflex image.

36. The method of claim 34, wherein said laser light comprises infrared laser light.

37. A method of capturing ocular reflex signals, comprising:
serially capturing a retinal reflex image of an ambient scene; and
serially capturing optical signals emanating from said ambient scene that have been ocularly, but non-retinally reflected by said eye.

38. The method of claim 37, further comprising:
generating deviation signals based on said captured optical signals;
correcting, based on said deviation signals, the zero position of a scan pattern to be described during a subsequent serial capture of a retinal reflex image.

39. A method of capturing a retinal reflex image of an ambient scene, comprising:
serially capturing retro-reflected optical signals emanating from said ambient scene from a plurality of retinal areas corresponding to one of a spiral scan pattern centered around the fovea centralis, and a scan pattern comprising a plurality of ellipses of sequentially increasing or decreasing size centered around the fovea centralis;
wherein size of selected retinal areas is smaller than size of other retinal areas more distant from said fovea centralis.

40. A method of capturing a retinal reflex image of an ambient scene, comprising:
serially capturing retro-reflected optical signals emanating from said ambient scene from a plurality of retinal areas corresponding to one of a spiral scan pattern centered around the fovea centralis, and a scan pattern comprising a plurality of ellipses of sequentially increasing or decreasing size centered around the fovea centralis;
wherein dwell time at selected retinal areas is shorter than dwell time at other retinal areas more distant from said fovea centralis.

41. A method of capturing a retinal reflex image of an ambient scene, comprising:
serially capturing retro-reflected optical signals emanating from said ambient scene from a plurality of retinal areas corresponding to one of a spiral scan pattern centered around the fovea centralis, and a scan pattern comprising a plurality of ellipses of sequentially increasing or decreasing size centered around the fovea centralis;
wherein dwell time at selected retinal areas differs from dwell time at other retinal areas more distant from said fovea centralis.

42. A method of capturing an integrated retinal reflex image of an ambient scene, comprising:
serially capturing a first retinal reflex image of an ambient scene;
serially capturing at least one subsequent retinal reflex images of said ambient scene; and
integrating said first captured retinal reflex image and said one subsequently captured retinal reflex images.

43. A method of capturing an integrated retinal reflex image of an ambient scene, comprising:
serially capturing a first retinal reflex image of an ambient scene from a first retina;
serially capturing a second retinal reflex image of said ambient scene from a second retina paired with said first retina; and integrating said first and second captured retinal reflex images.

44. A method of obtaining a perspective view of an ambient scene viewed by a pair of eyes, comprising:

simultaneously serially capturing respective retinal reflex images of said ambient scene from each of said eyes.

* * * * *